(12) United States Patent
Ackermann

(10) Patent No.: US 6,941,577 B2
(45) Date of Patent: Sep. 13, 2005

(54) ANTIGLARE DEVICE FOR WELDING PROTECTIVE MASKS

(75) Inventor: Emil Ackermann, Wattwil (CH)

(73) Assignee: Optrel AG, Wattwil (CH)

( * ) Notice: Subject to any disclaimer, the term of this patent is extended or adjusted under 35 U.S.C. 154(b) by 56 days.

(21) Appl. No.: 10/451,022

(22) PCT Filed: Dec. 18, 2001

(86) PCT No.: PCT/CH01/00724
§ 371 (c)(1),
(2), (4) Date: Jun. 19, 2003

(87) PCT Pub. No.: WO02/49554
PCT Pub. Date: Jun. 27, 2002

(65) Prior Publication Data
US 2005/0097648 A1 May 12, 2005

(30) Foreign Application Priority Data
Dec. 21, 2000 (CH) ................................... 2494/00

(51) Int. Cl.[7] .............................. A42B 1/00; G02F 1/00
(52) U.S. Cl. ............................. 2/8; 250/201.1; 349/14
(58) Field of Search ............................. 2/8; 250/201.1; 349/14; 219/147, 132

(56) References Cited

U.S. PATENT DOCUMENTS

| | | | | |
|---|---|---|---|---|
| 4,039,803 A | * | 8/1977 | Harsch | 219/147 |
| RE29,684 E | * | 6/1978 | Gordon | 219/147 |
| 4,130,903 A | * | 12/1978 | VAN DEN Berg et al. | 2/8 |
| 4,155,122 A | * | 5/1979 | Budmiger | 2/8 |
| 4,446,354 A | * | 5/1984 | Kearney | 219/130.01 |
| 4,560,239 A | * | 12/1985 | Katz | 349/14 |
| 4,620,322 A | | 11/1986 | Eggenschwiler et al. | |
| 4,638,146 A | * | 1/1987 | Koyama | 219/147 |
| 4,679,255 A | * | 7/1987 | Kuhlman | 2/8 |
| 5,751,258 A | * | 5/1998 | Fergason et al. | 345/7 |
| 5,959,705 A | | 9/1999 | Fergason | |
| 6,008,466 A | * | 12/1999 | Hosoda | 219/121.62 |
| 6,270,223 B1 | * | 8/2001 | Del Bon et al. | 359/601 |
| 6,552,316 B1 | * | 4/2003 | Bae | 250/201.1 |

FOREIGN PATENT DOCUMENTS

| | | | |
|---|---|---|---|
| EP | 0027518 A1 | * | 4/1981 |
| FR | 2 530 039 A | | 1/1984 |

OTHER PUBLICATIONS

WO 99/12060, Apparatus and Method for Protection Eyes From Ultraviolet and Bright Visible Light, Publication Date: Mar. 11, 1999.
WO 97/15256, A Liquid Crystal Shutter and a Light Shielding Device Including Such a Shutter, Publication Date: May 1, 1997.

* cited by examiner

*Primary Examiner*—Rodney M. Lindsey
(74) *Attorney, Agent, or Firm*—Rankin, Hill, Porter & Clark LLP

(57) ABSTRACT

A glare protection device for a welding protective mask includes an active electro-optical protective filter (2) and an electronic circuit (10). An UV-detector (UVD), which serves as an optical sensor, detects the welding light and, via an evaluation circuit (10.1), generates a signal (sin) for controlling of the protective filter (2). The signal corresponds to the detected UV intensity. The UV-detector includes a fluorescent layer (F) with an absorption in the UV range and an emission in the long-wave range corresponding to the spectral sensitivity of an assigned Si-photo detector (SD). This results in a simple and safe controlling of the protective filter, which is uninfluenced by the effects of extraneous light.

19 Claims, 3 Drawing Sheets

ANTIGLARE DEVICE FOR WELDING PROTECTIVE MASKS

BACKGROUND OF THE INVENTION

The present invention is generally related to a glare protection device for welding protective masks and to a method for controlling a glare protection device. The present invention is further directed toward a glare protection device including an active electro-optical protective filter, an electronic circuit, and an optical sensor, and toward a method for controlling such a glare protection device.

Glare protection devices of the aforementioned type are generally known from, for example, WO98/57606 or the EP 0 550 384, wherein an optical sensor for the detection of the welding light by means of an active electronic circuit switches an active electro-optical protective filter such that, when welding light occurs, immediately a predefined blacking out level (protection level) is switched on. Similarly, when the welding light stops, the blacking out is immediately switched off again.

Modern glare protection devices of this kind, in particular as sight window for welding protective masks, as the active filter element typically include a liquid crystal cell, which blocks the passage of light to a greater or lesser extent, as soon as the light intensity detected by a sensor exceeds a predefined threshold. In doing so, an electronic circuit in the glare protection device comprises an evaluation circuit for the sensor output signal and a driving circuit for the liquid crystal cell.

For the detection of the radiation up until now usually silicon photo detectors have been utilised. Silicon photo detectors detect radiation in a wavelength range from red to the near infrared (NIR), i.e., within the range of, e.g., 600–900 nm. Every welding process has its own characteristic light spectrum, which, for example, is determined by the welding parameters (electric current, gas, materials) and the welding process. In the case of practically all welding processes, the proportion of the emitted radiation in the UV range is great, while in the red—and NIR range a relatively small proportion is emitted. On the other hand, however, by extraneous light, e.g., by artificial light, a relatively large proportion is emitted in the long-wave range, i.e., in the NIR—and red range, while the UV proportion of artificial light is relatively small. For this reason, within the sensitivity range of the silicon detectors utilised up to now a relatively small proportion of the welding light and in contrast, however, a great proportion of extraneous—and stray light is detected, which renders the differentiation of the welding light from this stray light exceedingly difficult.

In order now to be in a position to differentiate the welding light from the extraneous light and from any possible stray light effects for the purpose of driving the protective filter, a very elaborate electronic circuit is required. In this, in particular to so-called flickering light from the electric welding arc is utilised for the separation of the welding light from extraneous light. In the case of an insufficient differentiation of the welding light from the extraneous light a malfunction occurs, i.e., that the blacking out does not switch on when welding light occurs, because the extraneous light sources are dominant. Similarly, insufficient differentiation also may prevent the blacking out from being switched off when the welding light ceases. In the case of the evaluation circuits in use today therefore so-called flickering light circuits are made use of, which detect the flickering light of the welding light within a certain frequency range, filter it out, and utilise it for the evaluation. The signal to noise ration here, however, is very poor, so that flickering light circuits of this type are exceedingly sensitive, elaborate, and subject to interferences.

SUMMARY OF THE INVENTION

It is an objective of the present invention to create a glare protection device, which overcomes these disadvantages prevailing up until now, which is less sensitive against the effects of extraneous light, and which makes possible a more simple, better and safer controlling of the protective filters without any malfunction.

In accordance with the invention the glare protection device incorporates an optical sensor that is a UV-detector having a sensor evaluation circuit that generates a signal for controlling of the protective filter and which corresponds to the UV intensity. With the optical sensor designed as a UV-detector, directly and to a great extent, the actual welding light is detected, while in correspondence with the relatively smaller UV proportion of extraneous light and stray light effects their influence is small. With the detection and evaluation of the measured UV intensity by a corresponding evaluation circuit, for the controlling of the protective filter a relatively simple, insensitive, and safe against interfering influences switching of the protective filter is achieved. The UV-detector comprises a fluorescent layer and an assigned Si-photo detector.

In particular, with the device and method according to the present invention a more simple, safer, and better electronic circuit for the controlling of the protective filters is able to be utilised. Thus, it is possible to make do without an elaborate and very sensitive flickering light detection—and evaluation in the electronic circuit.

The present invention further provides benefits with respect to simplicity, operational safety, optimum adjustability of the blacking out and universal usability as well as additional advantages in the handling of glare protection devices of this kind.

BRIEF DESCRIPTION OF THE DRAWINGS

These and further features of the present invention will be apparent with reference to the following description and drawings, wherein.

DETAILED DESCRIPTION OF THE PREFERRED EMBODIMENTS

Figure 1:
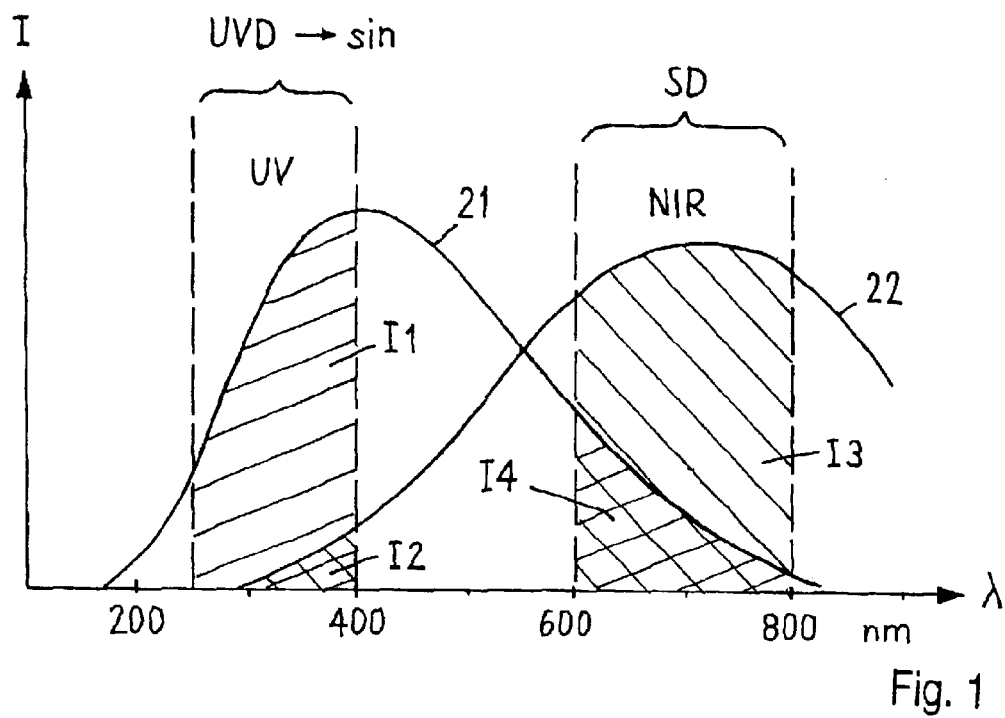
FIG. 1 illustrates the differentiation between welding light and extraneous light according to the invention by means of a spectral intensity distribution.

FIG. 1 schematically illustrates the spectral intensity distributions I($\lambda$) for a welding light 21 with a high intensity proportion in the short-wave range and for an artificial light source as extraneous light 22 with a high proportion in the long-wave range. The welding light comprises a high intensity proportion I1 in the UV range, which is detected by a UV-detector UVD. The artificial light in contrast comprises a high intensity proportion I3 in the red range NIR, which is detected by a conventional Si-photo sensor SD. In the UV range the artificial light 22 comprises a small intensity proportion I2, while vice-versa the welding light 21 comprises a small intensity proportion I4 in the NIR range.

The UV-detector UVD, e.g., detects a short-wave range of 250–400 nm and the Si-photo detector SD a long-wave range of, e.g., 600–900 nm. With Si-sensors SD used up to now, therefore a relatively poor intensity ration I4/I3 of welding light to extraneous light is detected, while with the UV-detector UVD in accordance with the invention a particularly favourable intensity ratio I1/I2 is able to be detected for the evaluation.

It is the idea of the invention to as directly as possible detect the welding light using simple means, so that it is only to a small extent superimposed by extraneous light influences. For this purpose the present invention utilises a spectrally selective photo detector in a particularly favourable spectral range and, with this selective detection of the welding light, controls the blacking out of the protective filter in a simple, safe, and optimum manner. For this, a UV-detector is provided which comprises a fluorescent layer F and an assigned Si-photo detector SD, as is further described in FIG. 3.

Figure 2:
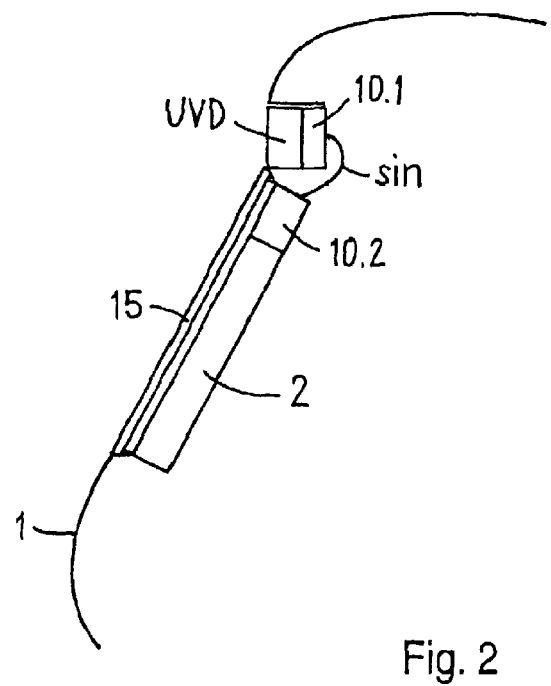
FIG. 2 illustrates a glare protection device in accordance with the invention with a UV-detector on a welding protective mask.

FIG. 2 depicts a glare protection device in accordance with the invention on a welding protective mask 1 with an active electro-optical protective filter 2. Serving as optical sensor here is a UV-detector UVD, which in a sensor evaluation circuit 10.1 generates a signal "sin" corresponding to the UV-intensity for the controlling of the protective filter 2.

The spectral sensitivity of the UV-detector is preferably designed such that radiation in a wave-length range of, e.g., 200–400 nm or also of 250–400 nm is detected.

Figure 3:
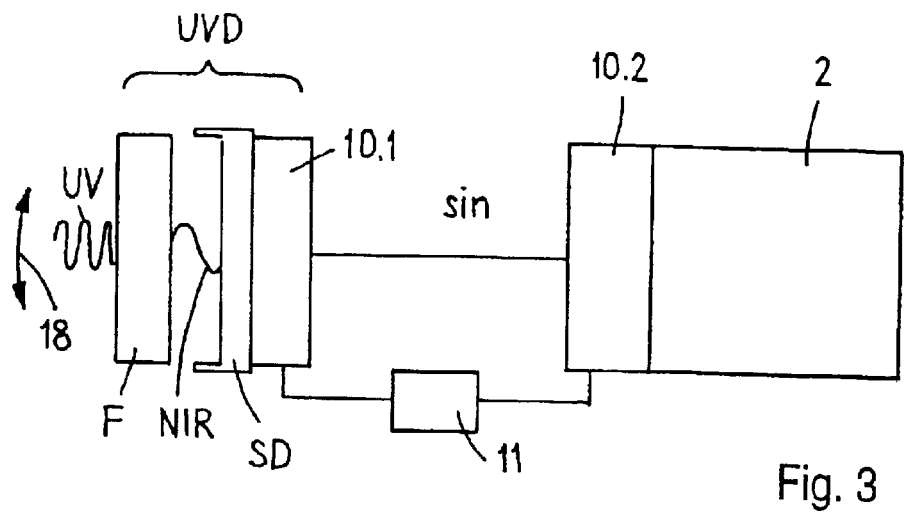
FIG. 3 illustrates a UV-detector with fluorescent layer and Si-photo detector.

FIG. 3 illustrates the concept of a UV-detector according to the invention that comprises a fluorescent layer F and an assigned Si-photo detector SD. The fluorescent layer provides an absorption in the UV range and an emission in the long-wave range in correspondence with the spectral sensitivity of the Si-photo detector SD. The absorption of the fluorescent layer F lies, for example, in the range of 200–400 nm and the emission in the range of 600–800 nm or of 600–900 nm. This signifies that the fluorescent layer is selected such that the short-wave UV welding light is converted into long-wave, easy to detect NIR light, which is capable of being detected by conventional, known Si-photo detectors. In doing so, the sensor evaluation circuit 10.1 generates a signal sin, which corresponds to the detected UV-intensity and with which, by means of a simple driving circuit 10.2, the protection filter 2 is able to be controlled corresponding to this signal sin of the UV-detector. This makes possible a simple, insensitive electronic circuit 10, which does not call for an elaborate and delicate flickering light detection and—evaluation in the NIR range. On the other hand, however, a flickering light detection in the UV range is also capable of being implemented in a much more simple manner thanks to the favourable intensity ratios, and thanks to a good signal to noise ratio. The complete control system of the protective filter therefore comprises the partial circuits 10.1 and 10.2, which are also able to be combined in an electronic circuit 10. Thanks to the better detection of the welding light in accordance with the invention, this method would be capable of being utilised not only in the case of electrical welding processes but also, for example, in the case of gas welding.

The embodiments of the UV-detector UVD as a separate unit make it possible to also geographically separate the UV-sensor, or here the fluorescent layer F from the glare protection holder and with this to be able to optimally position and align it.

Figure 4:
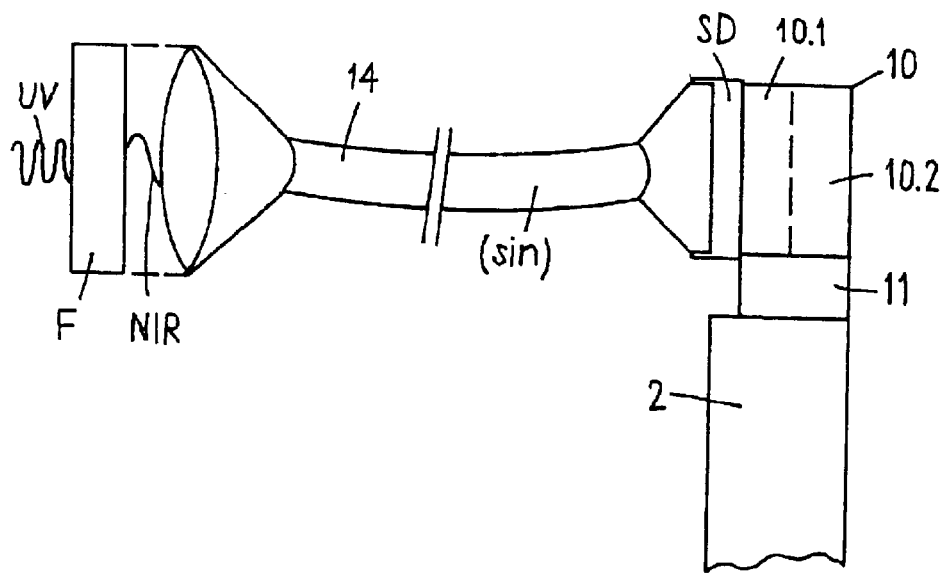
FIG. 4 illustrates a UV-detector with a fluorescent layer, wave-guide and Si-photo detector.

An example of an embodiment for this is illustrated in FIG. 4. Here the UV-detector is formed by the fluorescent layer F with a lens system as input into a fibre-glass wave-guide 14, which transmits the transformed NIR radiation to the Si-detector SD (while wave-guides are not suitable for the transmission of UV radiation). This separate UV-sensor does not require its own electric power supply. The complete electronic circuit (10.1 and 10.2) together with the necessary electric power supply 11 is attached to the glare protection holder.

Figure 5:
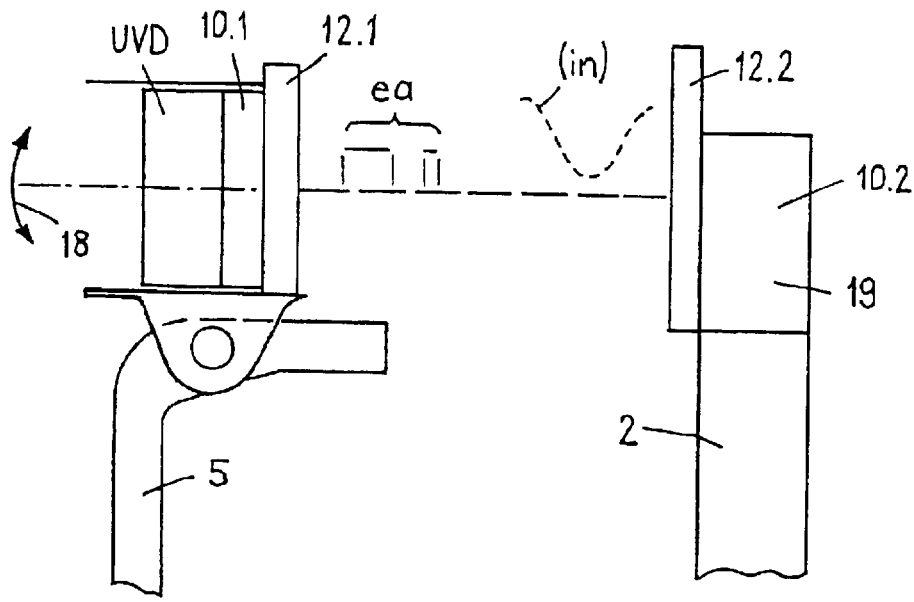
FIG. 5 illustrates a separate UV-detector with wireless signal transmission.

FIG. 5 illustrates a further possibility of geographically separating the UV-detector UVD from the glare protection holder. This embodiment comprises two parts, which are connected to one another wirelessly (RF). The first part is formed by the UV-detector UVD with the sensor evaluation circuit 10.1 and with an RF transmitter 12.1. The second part is formed by an RF receiver 12.2 with a driving circuit 10.2 for the protective filter 2. With this embodiment, from the RF transmitter part 12.1 an intensity signal "in" corresponding to the detected UV intensity is able to be generated and wirelessly transmitted to the glare protection holder. In a further variant of the embodiment on the transmitter part by means of a corresponding signal evaluation circuit 10.1 also only a simple on/off signal "ea" is capable of being generated, which is easy to transmit and which on the RF receiver 12.2 switches the blacking out of the protective filter on and off.

As these examples illustrate, the UV-detector UVD in accordance with the invention is also able to be arranged outside the protective mask, in particular closer to the welding point, for example on the welding device, or on its hand-protection 5. Here the intensity of the detected welding light is significantly higher than at the protective mask and the extraneous light influence is correspondingly relatively smaller. This once again improves the controlling of the protective filter 2.

If the UV-detector is separately positioned and there are differing distances between the welding light and the eye, and between the welding light and the UV-detector, then these differences can be taken into account with a distance compensation 19 in the electronic circuit 10.

Up until now the blacking out took place to a fixed pre-defined, or a fixed set protection level N, i.e., the transmission of the protective filter 2 is reduced to a fixed, low value corresponding to the protection level. Thanks to the more accurate detection of the welding light in accordance with the invention, however, now also an automatic controlling of the blacking out, i.e., a controlling of the degree of transmission of the protective filter in function of the detected UV radiation intensity is capable of being implemented. In doing so, e.g., a pre-definable minimum protection level value Nmin is able to be set and above this within a variation range of, e.g., two to four further protection levels the transmission is able to be follow-up controlled reduced, therefore, e.g., a set minimum protection level Nmin=9 and a reduced follow-up control within a range of N=9–12, wherein the weighting of the UV intensity for this controlling of the protective filter transmission is basically capable of being selected.

Figure 6:
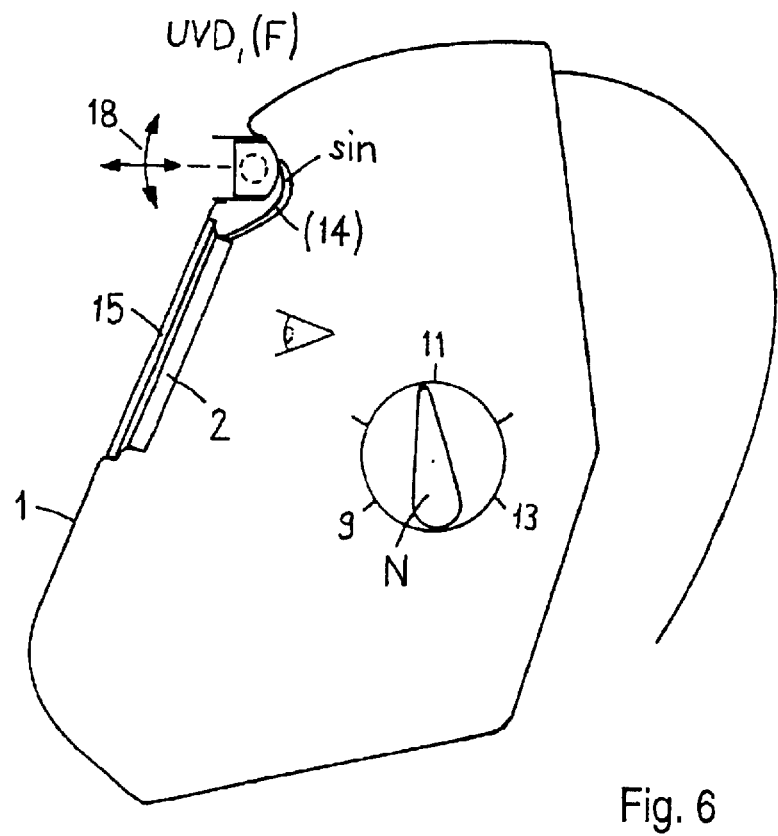
FIG. 6 illustrates an example of an adjustable glare protection device on a welding protective mask.

FIG. 6 illustrates a welding protective mask 1 with a glare protection device, which comprises a separate, orientable UV-detector UVD. This capability of being oriented is indicated with the arrows 18 (the same as in FIG. 5 or FIG. 3). The UV-detector here is separately attached to the helmet above the protective filter 2 and, for example, is connected with the protective filter 2, or with the glare protection holder through a wave-guide 14. In this it is of importance that the UV-detector is situated outside a protection glass 15 (the same as in the example of FIG. 2). With this, a UV absorption by the protection glass 15, which is made of, for example, poly-carbonate, cannot impair the function of the UV-detector. The example of FIG. 6 also depicts an as such known, additional manual protection level adjustment, e.g., within a range of N=9–13, which in combination with the protective filter control according to the invention provides further advantages in application.

Within the framework of this application, the following terms and designations are used:

1 Welding protective mask
 2 Active electro-optical protective filter (glare protection holder)
 5 Hand protection, welding device
 10 Electronic circuit
 10.1 Sensor evaluation circuit
 10.2 Driving circuit for 2
 11 Electric power supply
 12.1 RF-transmitter
 12.2 RF-receiver
 14 Fibre-glass wave-guide
 15 Protection glass for 2
 18 Orientable, adjustable
 19 Distance compensation
 21 Welding light
 22 Artificial light, extraneous light
 N Protection level value
 UVD UV radiation detector
 F Fluorescent layer
 SD Si-photo detector
 I Light intensity
 λ Wave-length
 UV UV range, short-wave
 NIR NIR—and red range, long-wave
 sin Intensity signal
 ea Wireless signal: on/of
 in Wireless signal: intensity

What is claimed is:

1. A glare protection device for a welding protective mask with an active electro-optical protective filter (2), an electronic circuit (10), and a UV-detector (UVD) as an optical sensor with a sensor evaluation circuit (10.1), said sensor evaluation circuit generating a signal (sin) for controlling of the protective filter (2), said signal (sin) corresponding to a UV intensity and wherein the UV-detector comprises a fluorescent layer and an assigned silicon photo detector (SD) and wherein the fluorescent layer is adapted to absorb light in the UV range and to emit light in a long-wave range corresponding to a spectral sensitivity of the Si-photo detector (SD).

2. The glare protection device according to claim 1, wherein the UV-detector (UVD) detects radiation in a wave-length range of 200–400 nm.

3. The glare protection device according to claim 1, wherein the absorption of the fluorescent layer (F) lies within a range of 200–400 nm and the emission within a range of 600–800 nm.

4. The glare protection device according to claim 1, wherein the fluorescent layer (F) is connected with the Si-photo detector (SD) through a glass-fiber wave guide (14).

5. The glare protection device according to claim 1, wherein the electronic circuit (10) comprises a driving circuit (10.2), said driving circuit utilizing the signal (sin) of the UV-detector for controlling the protective filter (2).

6. The glare protection device according to claim 1, wherein the electronic circuit (10) does not comprise a flickering light detection and evaluation system.

7. The glare protection device according to claim 1, wherein the sensor evaluation circuit (10.1) further comprises an RF-transmitter (12.1) and that, separate from said RF-transmitter, on the welding protective mask (1) an RF-receiver (12.2) with a driving circuit (10.2) for the protective filter (2) is disposed.

8. The glare protection device according to claim 7, wherein, in the RF-transmitter (12.1), a wireless on/off signal (ea) is generated.

9. The glare protection device according to claim 7, wherein, in the RF-transmitter (12.1), an intensity signal (in) is generated.

10. The glare protection device according to claim 1, wherein the UV-detector (UVD) is situated on the protective mask (1) outside a protection glass (15).

11. The glare protection device according to claim 1, wherein the UV-detector is arranged outside the protective mask (1).

12. The glare protection device according to claim 1, wherein the UV-detector (UVD) is arranged on an assigned welding device (5).

13. The glare protection device according to claim 12, wherein the UV-detector (UVD) is arranged on a hand protection device.

14. The glare protection device according to claim 1, wherein the UV-detector (UVD) is adapted to be adjusted to the welding light (18).

15. The glare protection device according to claim 1, wherein, in the case of differing distances between the welding light and the eye and the welding light and the UV-detector in the electronic circuit (10), a distance compensation element (19) is provided.

16. The glare protection device according to claim 1, wherein an automatic controlling of the blacking out of the protective filter (2) in function of the detected UV radiation intensity is provided.

17. The glare protection device according to claim 16, wherein the blacking out sets at least a pre-definable protection level value (Nmin) and over and above this comprises a reduced follow-up control within a variation range of between about 2–3 protection levels.

18. The glare protection device according to claim 16, wherein, in addition, a manual protection level setting (N) is provided.

19. A method for controlling of a glare protection device of a welding protective mask with an active electro-optical filter (2) and an electronic circuit (10), comprising the steps of: detecting UV light with an optical UV-detector (UVD), generating a signal (sin) with a sensor evaluation circuit (10.1.), said signal corresponding to an intensity of the UV light, and using said signal to control the protective filter (2) and wherein the UV-detector comprises a fluorescent layer and an assigned silicon photo detector (SD) and wherein the fluorescent layer is adapted to absorb light in the UV range and to emit light in a long-wave range corresponding to a spectral sensitivity of the Si-photo detector (SD).

* * * * *